(12) United States Patent
Michihata

(10) Patent No.: US 11,483,489 B2
(45) Date of Patent: Oct. 25, 2022

(54) MEDICAL CONTROL DEVICE AND MEDICAL OBSERVATION SYSTEM USING A DIFFERENT WAVELENGTH BAND THAN THAT OF FLUORESCENCE OF AN OBSERVATION TARGET TO CONTROL AUTOFOCUS

(71) Applicant: Sony Olympus Medical Solutions Inc., Tokyo (JP)

(72) Inventor: Taihei Michihata, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/169,603

(22) Filed: Feb. 8, 2021

(65) Prior Publication Data

US 2021/0297575 A1 Sep. 23, 2021

(30) Foreign Application Priority Data

Mar. 18, 2020 (JP) .............................. JP2020-047500

(51) Int. Cl.
*H04N 5/235* (2006.01)
*H04N 5/225* (2006.01)
*A61B 1/06* (2006.01)
*A61B 1/04* (2006.01)
*H04N 9/73* (2006.01)
(Continued)

(52) U.S. Cl.
CPC ........... *H04N 5/2354* (2013.01); *A61B 1/043* (2013.01); *A61B 1/0638* (2013.01); *H04N 5/2256* (2013.01); *H04N 5/2351* (2013.01); *H04N 9/71* (2013.01); *H04N 9/735* (2013.01); *H04N 7/183* (2013.01); *H04N 2005/2255* (2013.01)

(58) Field of Classification Search
CPC ........ A61B 1/043; A61B 1/0638; H04N 9/71; H04N 9/735; H04N 5/2256
See application file for complete search history.

(56) References Cited

U.S. PATENT DOCUMENTS

2012/0248333 A1* 10/2012 Fallert ................. G01N 21/6456
 250/208.1
2014/0350395 A1* 11/2014 Shachaf ........... H04N 5/232122
 600/431

(Continued)

FOREIGN PATENT DOCUMENTS

WO WO-2018178269 A1 * 10/2018 ........... A61B 3/1025
WO WO-2021019597 A1 * 2/2021

*Primary Examiner* — Jayanti K Patel
*Assistant Examiner* — Christopher Kingsbury Glover
(74) *Attorney, Agent, or Firm* — Xsensus LLP

(57) ABSTRACT

A medical control device includes circuitry configured to: control an autofocus operation on a captured image from an observation target illuminated with excitation light of a first wavelength band and a pattern image of a second wavelength band, the observation target fluorescing in response to the excitation light to output light in a third wavelength band. The captured image includes light components in the first to third wavelengths bands, of which the second and third wavelength bands are different. The autofocus operation is controlled by calculating, based on the pattern image of the second wavelength band in the captured image, an evaluation value used in an autofocus process that controls a focus position of an imaging device configured to generate the captured image.

16 Claims, 11 Drawing Sheets

(51) Int. Cl.
*H04N 7/18* (2006.01)
*H04N 9/71* (2006.01)

(56) References Cited

U.S. PATENT DOCUMENTS

| | | | | |
|---|---|---|---|---|
| 2018/0279864 A1* | 10/2018 | Frangioni | ............ | A61B 5/0071 |
| 2019/0361216 A1* | 11/2019 | Berretta | ................ | H04N 9/735 |
| 2019/0379840 A1* | 12/2019 | Frangioni | ............ | A61B 1/0638 |

* cited by examiner

MEDICAL CONTROL DEVICE AND MEDICAL OBSERVATION SYSTEM USING A DIFFERENT WAVELENGTH BAND THAN THAT OF FLUORESCENCE OF AN OBSERVATION TARGET TO CONTROL AUTOFOCUS

This application claims priority from Japanese Application No. 2020-047500, filed on Mar. 18, 2020, the contents of which are incorporated by reference herein in its entirety.

BACKGROUND

The present disclosure relates to a medical control device and a medical observation system.

In the related art, there is known a photodynamic diagnosis apparatus for performing photodynamic diagnosis (PDD), which is one of cancer diagnosis methods of detecting cancer cells (see, for example, JP 2016-202726 A).

In photodynamic diagnosis, for example, a photosensitive substance such as 5-aminolevulinic acid (hereinafter, referred to as "5-ALA") is used. The 5-ALA is a natural amino acid originally contained in the living bodies of animals and plants. This 5-ALA is taken into cells after administration into the body and biosynthesized into protoporphyrin in mitochondria. Meanwhile, the protoporphyrin is excessively accumulated in cancer cells. In addition, the protoporphyrin that excessively accumulates in the cancer cells has photoactivity. Consequently, when the protoporphyrin is excited with excitation light (for example, blue visible light in wavelength band of 375 nm to 445 nm), the protoporphyrin emits fluorescence (for example, red fluorescence in wavelength band of 600 nm to 740 nm). As described above, the cancer diagnosis method in which a photosensitive substance is used to cause cancer cells to emit fluorescence is called photodynamic diagnosis.

The photodynamic diagnosis apparatus disclosed in JP 2016-202726 A includes a fluorescence capturing device that captures fluorescence from a photosensitive substance excited by excitation light to generate a fluorescence captured image and an optical filter that is disposed so as to precede the fluorescence capturing device in its optical path and cuts all excitation light directed toward the fluorescence capturing device.

SUMMARY

The fluorescence captured image has a very low signal level because the amount of fluorescence from a photosensitive substance is very small.

For this reason, even if the evaluation value used in an autofocus (AF) process that controls the focus position of an image capturing unit is calculated based on the fluorescence captured image, an appropriate evaluation value may not be calculated.

Here, it is conceivable that the excitation light component is made to be included in the fluorescence captured image by transmitting a part of excitation light directed toward a fluorescence capturing device, instead of cutting all the excitation light by an optical filter. However, the excitation light is not in the green wavelength band that contributes to the brightness, but in the blue wavelength band that hardly contributes to the brightness. Consequently, even if the evaluation value described above is calculated based on the fluorescence captured image including the excitation light component, an appropriate evaluation value may not be calculated as in the above case.

As a result, there is a problem that the AF process may not be appropriately performed because the evaluation value is not appropriate, and an image suitable for observation may not be generated.

There is a need for a medical image processing apparatus and a medical observation system that generate an image suitable for observation.

According to one aspect of the present disclosure, there is provided a medical control device including circuitry configured to: control an operation of a light source device configured to emit excitation light in a first wavelength band and image light including a specific pattern image; acquire a captured image obtained by capturing an observation target irradiated with light emitted from the light source device; calculate, based on the captured image, an evaluation value used in an autofocus process that controls a focus position of an imaging device configured to generate the captured image; and perform the autofocus process based on the evaluation value, wherein the circuitry is configured to control the operation of the light source device such that the pattern image is included in the captured image used for calculating the evaluation value.

DETAILED DESCRIPTION

Figure 1:
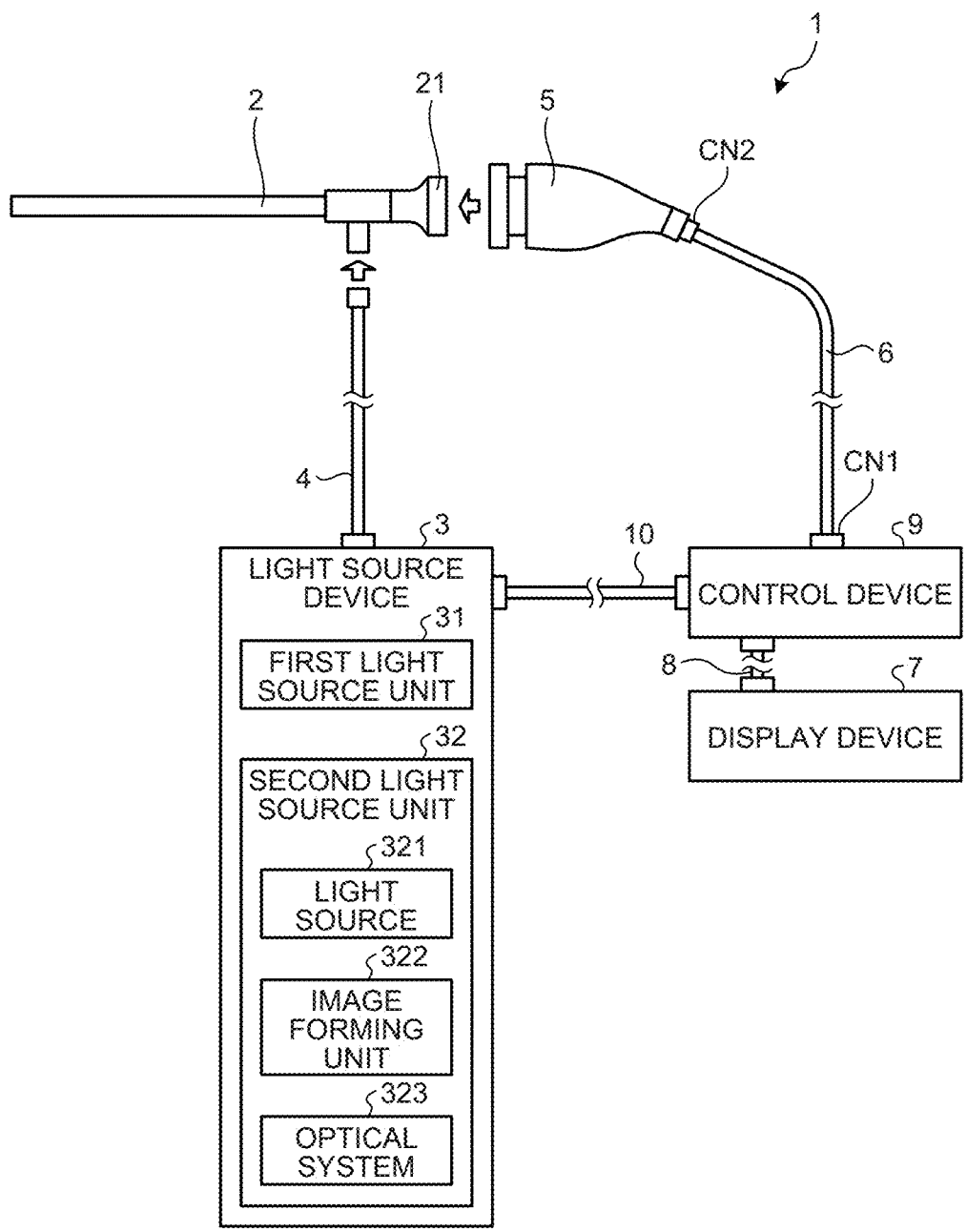
FIG. 1 is a view illustrating a configuration of a medical observation system according to a first embodiment.

Hereinafter, modes for carrying out the present disclosure (hereinafter, "embodiments") will be described with reference to the drawings. The present disclosure is not limited by the embodiments to be described below. In addition, in the description of the drawings, the same parts are designated by the same reference numerals.

First Embodiment

Schematic Configuration of Medical Observation System

FIG. 1 is a view illustrating a configuration of a medical observation system 1 according to a first embodiment.

The medical observation system 1 is used in the medical field and captures (observes) the inside of a living body (observation target) as a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 is composed of a rigid endoscope. That is, the insertion unit 2 has an elongated shape in which the whole part is rigid, or a part is flexible and the other part is rigid, and the insertion unit 2 is inserted into the living body. The insertion unit 2 includes an optical system that is composed of one or a plurality of lenses and focuses light from the subject.

Figure 2:
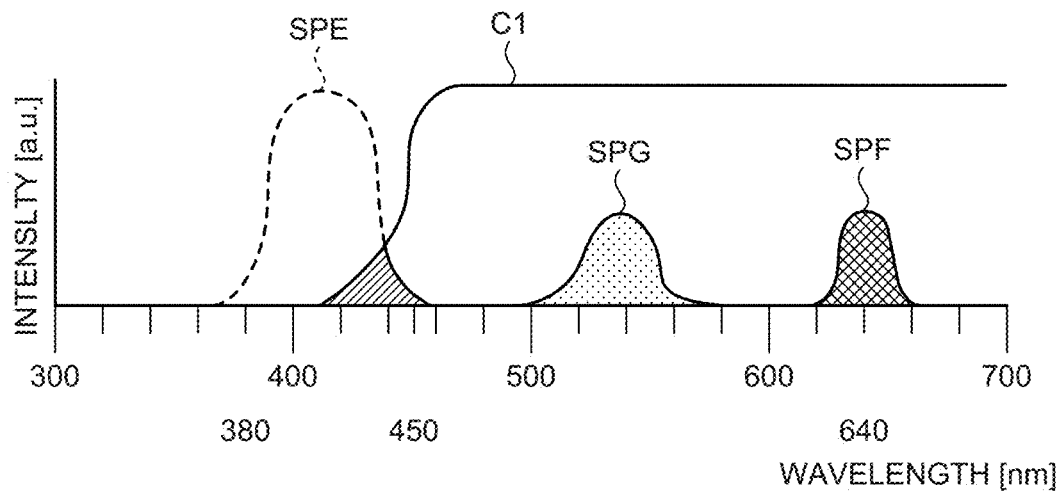
FIG. 2 is a diagram illustrating a spectrum of light emitted from a light source device.

FIG. 2 is a diagram illustrating a spectrum of light emitted from the light source device 3.

The light source device 3 supplies light for illuminating the inside of the living body to one end of the light guide 4 under the control of the control device 9. In the first embodiment, the light source device 3 includes a first light source unit 31 and a second light source unit 32, as illustrated in FIG. 1.

The first light source unit 31 is composed of an LED (Light Emitting Diode), a semiconductor laser, or the like, and emits excitation light in a first wavelength band. In the first embodiment, the excitation light in the first wavelength band is excitation light in the blue wavelength band (for example, wavelength band of 375 nm to 445 nm) that excites protoporphyrin, like a spectrum SPE illustrated in FIG. 2. When excited by the excitation light, the protoporphyrin emits fluorescence in the red wavelength band (for example, wavelength band of 600 nm to 740 nm) like a spectrum SPF illustrated in FIG. 2.

Figure 3:
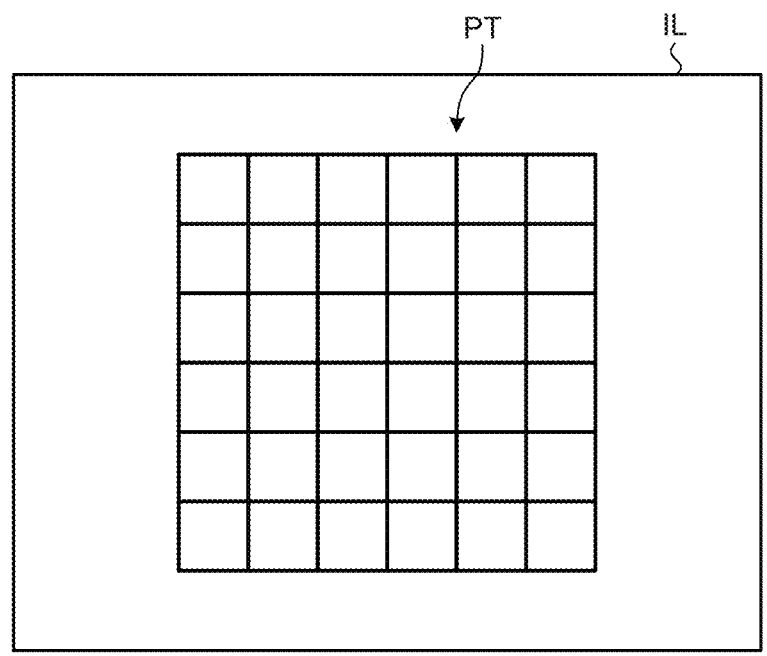
FIG. 3 is a view illustrating an example of image light emitted from a second light source unit.

FIG. 3 is a view illustrating an example of image light IL emitted from the second light source unit 32.

As illustrated in FIG. 3, the second light source unit 32 emits the image light IL including a pattern image PT. As illustrated in FIG. 1, the second light source unit 32 includes a light source 321, an image forming unit 322, and an optical system 323.

The light source 321 is composed of an LED, a semiconductor laser, or the like, and emits light in a second wavelength band. In the first embodiment, the light in the second wavelength band is light in the green wavelength band (for example, wavelength band of 500 nm to 560 nm), like a spectrum SPG illustrated in FIG. 2. That is, the light in the second wavelength band is a narrow band light that does not include the wavelength band of fluorescence described above.

The image forming unit 322 is composed of a digital mirror device (DMD), a liquid crystal panel, or the like, and under the control of the control device 9, modulates the light in the second wavelength band emitted from the light source 321 to generate the image light IL including the pattern image PT. Specifically, the pattern image PT is located in an area including the center of the image light IL, and is a grid image. Then, in the image light IL, the pattern image PT (grid portion) is composed of light in the second wavelength band, and the portion other than the grid is composed of black that does not include the light in the second wavelength band. In FIG. 3, the grid portion is represented by a black line, and the portion other than the grid is represented by white.

The optical system 323 supplies the image light IL formed by the image forming unit 322 to one end of the light guide 4.

Further, in the light source device 3 of the first embodiment, the first and second light source units 31 and 32 are simultaneously driven under the control of the control device 9. That is, the light source device 3 simultaneously emits the excitation light and the image light IL.

The light source device 3 is configured separately from the control device 9 in the first embodiment, but the present disclosure is not limited thereto, and the configuration in which the light source device 3 is provided in the control device 9 may be adopted.

The light guide 4 is removably connected to the light source device 3 at one end, and is also removably connected to the insertion unit 2 at the other end. The light guide 4 then transmits light emitted from the light source device 3 from one end to the other end to supply the light to the insertion unit 2. The emitted light (excitation light and image light IL) supplied to the insertion unit 2 is emitted from the distal end of the insertion unit 2 and is irradiated to the living body. The excitation light that is irradiated to the living body and reflected in the living body, the image light IL that is reflected in the living body, and the fluorescence emitted by exciting protoporphyrin that accumulates in lesions in the living body is focused by the optical system in the insertion unit 2. Hereinafter, for convenience of explanation, the excitation light, the image light IL, and the fluorescence focused by the optical system in the insertion unit 2 is referred to as "subject image".

The camera head 5 corresponds to an imaging device of the present disclosure. The camera head 5 is removably connected to a proximal end (eyepiece 21 (FIG. 1)) of the insertion unit 2. The camera head 5 then captures the subject image (excitation light, image light IL, and fluorescence) focused by the insertion unit 2 and outputs an image signal (RAW signal) obtained by such image capturing, under the control of the control device 9. The image signal is, for example, an image signal of 4K or higher.

The detailed configuration of the camera head 5 will be described later.

The first transmission cable 6 is removably connected to the control device 9 via a connector CN1 (FIG. 1) at one end, and is also removably connected to the camera head 5 via a connector CN2 (FIG. 1) at the other end. The first transmission cable 6 then transmits the image signal or the like output from the camera head 5 to the control device 9, and also transmits a control signal, a synchronization signal, a clock, power, and the like output from the control device 9 to the camera head 5.

In the transmission of the image signal or the like from the camera head 5 to the control device 9 through the first transmission cable 6, the image signal or the like may be transmitted as an optical signal or as an electric signal. The same holds true for the transmission of the control signal, the synchronization signal, and the clock from the control device 9 to the camera head 5 through the first transmission cable 6.

The display device 7 is composed of a displaying display using a liquid crystal, an organic EL (Electro Luminescence), or the like, and displays an image based on a video signal from the control device 9 under the control of the control device 9.

The second transmission cable 8 is removably connected to the display device 7 at one end, and is also removably connected to the control device 9 at the other end. The second transmission cable 8 then transmits the video signal processed by the control device 9 to the display device 7.

The control device 9 corresponds to the medical control device according to the present disclosure. The control device 9 is composed of a CPU (Central Processing Unit), an FPGA (Field-Programmable Gate Array), or the like, and comprehensively controls the operations of the light source device 3, the camera head 5, and the display device 7.

The detailed configuration of the control device 9 will be described later.

The third transmission cable 10 is removably connected to the light source device 3 at one end, and is also removably connected to the control device 9 at the other end. The third transmission cable 10 then transmits a control signal from the control device 9 to the light source device 3.

Configuration of Camera Head

Next, the configuration of the camera head 5 will be described.

Figure 4:
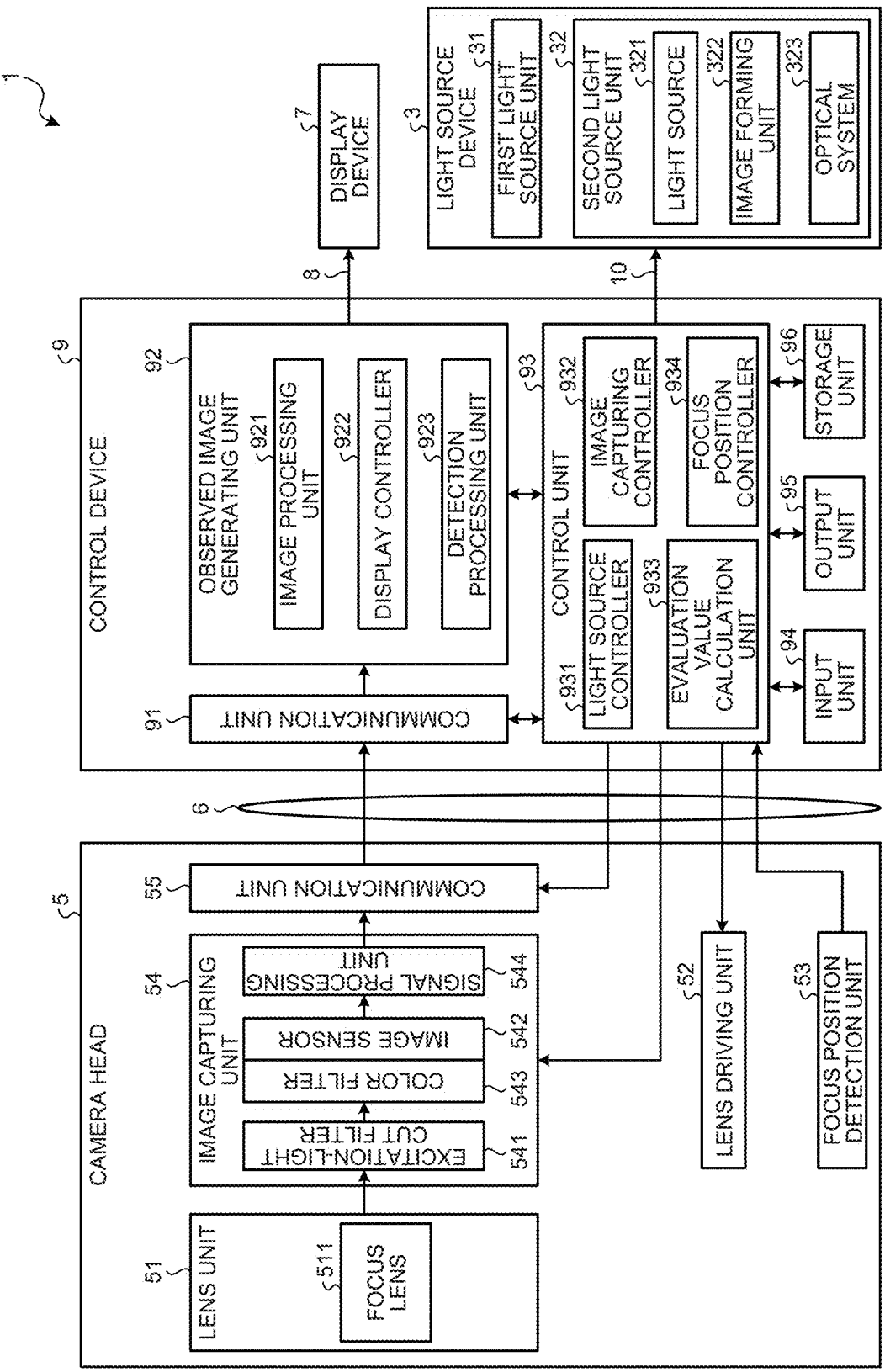
FIG. 4 is a block diagram illustrating a configuration of a camera head and a control device.

FIG. 4 is a block diagram illustrating a configuration of the camera head 5 and the control device 9.

In FIG. 4, for convenience of explanation, the connectors CN1 and CN2 between the control device 9 and the camera head 5, and the first transmission cable 6, and the connectors between the control device 9 and the display device 7, and the second transmission cable 8, and the connectors between the control device 9 and the light source device 3, and the third transmission cable 10 are not illustrated.

As illustrated in FIG. 4, the camera head 5 includes a lens unit 51, a lens driving unit 52, a focus position detection unit 53, an image capturing unit 54, and a communication unit 55.

The lens unit 51 includes a focus lens 511, and has a function of forming a subject image (excitation light, image light IL, and fluorescence) focused by the insertion unit 2 on an image capturing surface of the image capturing unit 54 (image sensor 542).

The focus lens 511 is composed of one or a plurality of lenses, and moves along an optical axis to adjust a focus position.

Further, the lens unit 51 includes a focus mechanism (not illustrated) that moves the focus lens 511 along the optical axis.

The lens driving unit 52 operates the focus mechanism described above under the control of the control device 9 to adjust the focus position of the lens unit 51 in the AF process performed by the control device 9, which will be described later.

The focus position detection unit 53 is composed of a position sensor such as a photo interrupter, and detects the current position (focus position) of the focus lens 511. The focus position detection unit 53 then outputs a signal corresponding to the detected focus position to the control device 9.

The image capturing unit 54 captures the inside of the living body under the control of the control device 9. As illustrated in FIG. 4, the image capturing unit 54 includes an excitation-light cut filter 541, the image sensor 542, a color filter 543, and a signal processing unit 544.

The excitation-light cut filter 541 is provided between the lens unit 51 and the image sensor 542, and has a transmission characteristic of transmitting light in a wavelength band of about 410 nm or more, as indicated by a curve C1 in FIG. 2. That is, the excitation-light cut filter 541 transmits all of the image light IL and fluorescence and a part of excitation light in the subject image (excitation light, image light IL, and fluorescence) directed from the lens unit 51 to the image sensor 542.

The image sensor 542 is composed of a CCD (Charge Coupled Device), a CMOS (Complementary Metal Oxide Semiconductor), or the like that receives light formed by the lens unit 51 and converts the light into an electric signal (analog signal). Hereinafter, for convenience of explanation, the captured image generated by capturing the subject image (excitation light, image light IL, and fluorescence) with the image sensor 542 is referred to as "PDD image".

Figure 5:
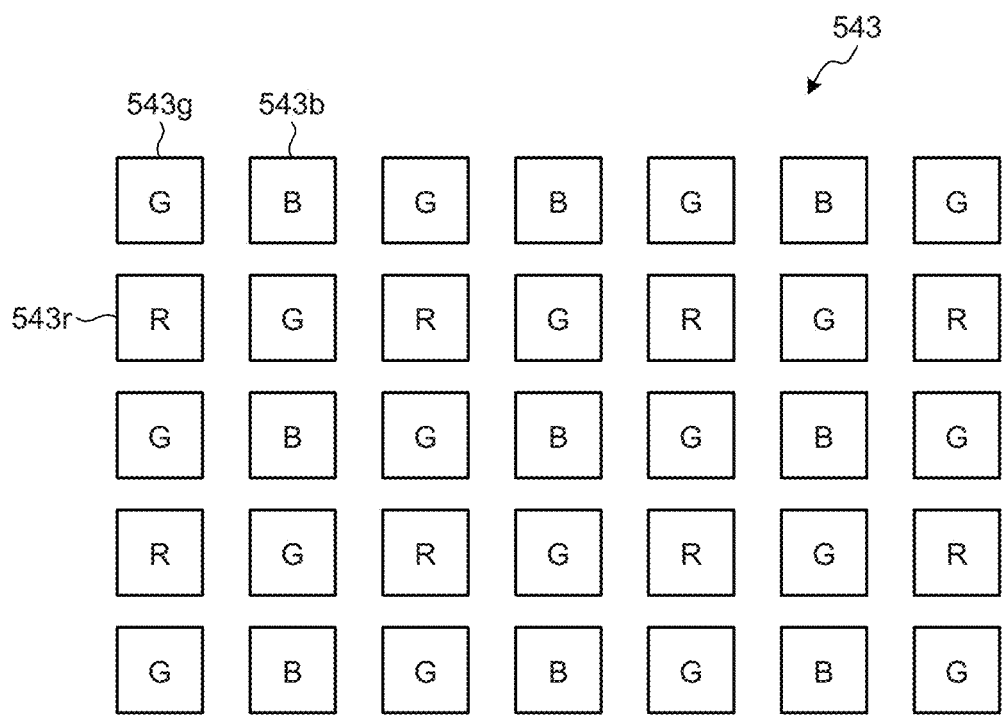
FIG. 5 is a diagram illustrating a color filter.

FIG. 5 is a diagram illustrating the color filter 543.

The color filter 543 is provided on the image capturing surface (light receiving surface) of the image sensor 542, and in the color filter 543, three filter groups grouped according to the wavelength band of light to be transmitted (R (red), G (green), B (blue)) are arranged in a specific format (for example, Bayer array).

Specifically, as illustrated in FIG. 5, the color filter 543 has an R filter group 543*r* that mainly transmits light in the red wavelength band, a B filter group 543*b* that mainly transmits light in the blue wavelength band, a first G filter group (arranged in same column as R filter group 543*r*) that mainly transmits light in the green wavelength band, and a second G filter group (arranged in same column as B filter group 543*b*) that mainly transmits light in the green wavelength band. In FIG. 5, the first and second G filter groups are collectively referred to as "G filter group 543*g*". Further, in FIG. 5, the letter "R" is attached to the R filter group 543*r*, the letter "G" is attached to the G filter group 543*g*, and the letter "B" is attached to the B filter group 543*b*.

The signal processing unit 544 performs signal processing on the PDD image (analog signal) generated by the image sensor 542 and outputs a PDD image (RAW signal (digital signal)) under the control of the control device 9.

For example, the signal processing unit 544 performs signal processing such as a process of removing reset noise, a process of multiplying an analog gain to amplify the analog signal, and A/D conversion on the PDD image (analog signal) generated by the image sensor 542.

The communication unit 55 functions as a transmitter that transmits a PDD image (RAW signal (digital signal)) output from the image capturing unit 54 to the control device 9 through the first transmission cable 6. The communication unit 55 is composed of, for example, a high-speed serial interface that communicates PDD images to the control device 9 at a transmission rate of 1 Gbps or more through the first transmission cable 6.

Configuration of Control Device

Next, the configuration of the control device 9 will be described with reference to FIG. 4.

As illustrated in FIG. 4, the control device 9 includes a communication unit 91, an observed image generating unit 92, a control unit 93, an input unit 94, an output unit 95, and a storage unit 96.

The communication unit 91 functions as a receiver that receives a PDD image (RAW signal (digital signal)) output from the camera head 5 (communication unit 55) through the first transmission cable 6. That is, the communication unit 91 corresponds to a captured image acquisition unit of the present disclosure. The communication unit 91 is composed of, for example, a high-speed serial interface that communicates PDD images to the communication unit 55 at a transmission rate of 1 Gbps or more.

The observed image generating unit 92 processes PDD images (RAW signals (digital signals)) that are sequentially output from the camera head 5 (communication unit 55) and received by the communication unit 91 under the control of the control unit 93. As illustrated in FIG. 4, the observed image generating unit 92 includes an image processing unit 921, a display controller 922, and a detection processing unit 923.

The image processing unit 921 performs first and second image processing on an input PDD image (RAW signal (digital signal)).

Examples of the first image processing include an optical black subtraction process, a white balance adjustment process, a digital gain process, a demosaic process, a color correction matrix process, a gamma correction process, and a YC process to convert an RGB signal (PDD image) into a luminance signal and a color difference signal (Y, $C_B/C_R$ signal).

In addition, the second image processing includes the adjustment process to be described below.

In the adjustment process, the component of light (image light IL) in the second wavelength band included in the PDD image is deleted. Specifically, the excitation light is light in the blue wavelength band (for example, wavelength band of 375 nm to 445 nm). Further, the image light IL is light in the green wavelength band (for example, wavelength band of 500 nm to 560 nm). In addition, fluorescence is light in the red wavelength band (for example, wavelength band of 600 nm to 740 nm). In the adjustment process, the G value, which is a component of the image light IL, is deleted from the R, G, and B pixel values included in the PDD image (G value is set to "0"), whereas the B value that is a component of the excitation light and the R value that is a component of fluorescence are left.

For example, in the white balance adjustment process, the G value among the R, G, and B pixel values included in the PDD image may be deleted by appropriately adjusting the gain to be multiplied by the R, G, and B pixel values. Further, in the demosaic process, for example, when the R value, the G value, and the B value are given to each pixel by interpolation, the G value among the R, G, and B pixel values included in the PDD image may be deleted. Furthermore, in the color correction matrix process, for example, the G value among the R, G, and B pixel values included in the PDD image may be deleted by appropriately adjusting a color correction matrix to be multiplied by an input matrix having the R, G, and B pixel values included in the PDD image as matrix elements.

That is, the image processing unit 921 corresponds to an adjustment process performing unit of the present disclosure.

The display controller 922 generates a video signal for displaying the PDD image subjected to the first and second image processing under the control of the control unit 93. The display controller 922 then outputs the video signal to the display device 7 through the second transmission cable 8.

The detection processing unit 923 performs the detection process based on the PDD image subjected to only the first image processing of the first and second image processing.

Specifically, the detection processing unit 923 performs, based on pixel information (for example, luminance signal (Y signal)) for each pixel in a detection area that is at least a part of the entire image area of the PDD image of one frame, detection of contrast and frequency components of an image in the detection region, detection of a luminance average value and maximum and minimum pixels in the detection area using a filter or the like, comparison with a threshold value, and detection of a histogram or the like (detection process). The detection processing unit 923 then outputs the detection information (contrast, frequency component, luminance average value, maximum and minimum pixels, histogram, and the like) obtained by the detection process to the control unit 93.

The control unit 93 is configured with, for example, a CPU, an FPGA, or the like, and outputs control signals through the first to third transmission cables 6, 8, and 10 to control the operation of the light source device 3, the camera head 5, and the display device 7 and the overall operation of the control device 9. As illustrated in FIG. 4, the control unit 93 includes a light source controller 931, an image capturing controller 932, an evaluation value calculation unit 933, and a focus position controller 934. The functions of the light source controller 931, the image capturing controller 932, the evaluation value calculation unit 933, and the focus position controller 934 will be described in "Operation of Control Device" to be described later.

The input unit 94 is configured with an operation device such as a mouse, a keyboard, or a touch panel, and accepts user operations by a user such as a doctor. The input unit 94 then outputs an operation signal corresponding to the user operation to the control unit 93.

The output unit 95 is configured with a speaker, a printer, or the like, and outputs various information.

The storage unit 96 stores a program executed by the control unit 93, information necessary for processing the control unit 93, and the like.

Operation of Control Device

Next, the operation of the control device 9 described above will be described.

Figure 6:
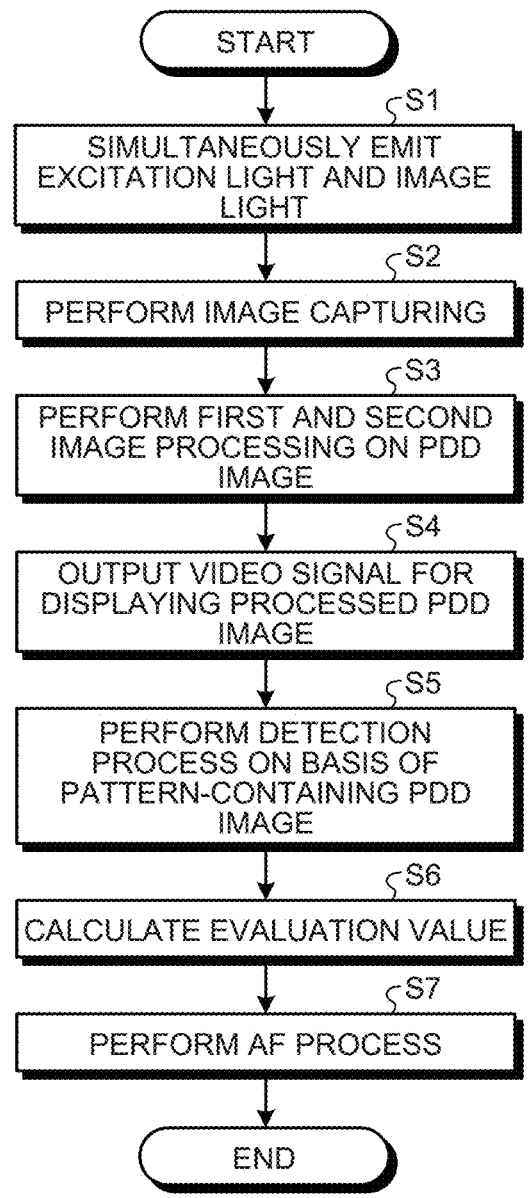
FIG. 6 is a flowchart illustrating an operation of the control device.
Figure 7:
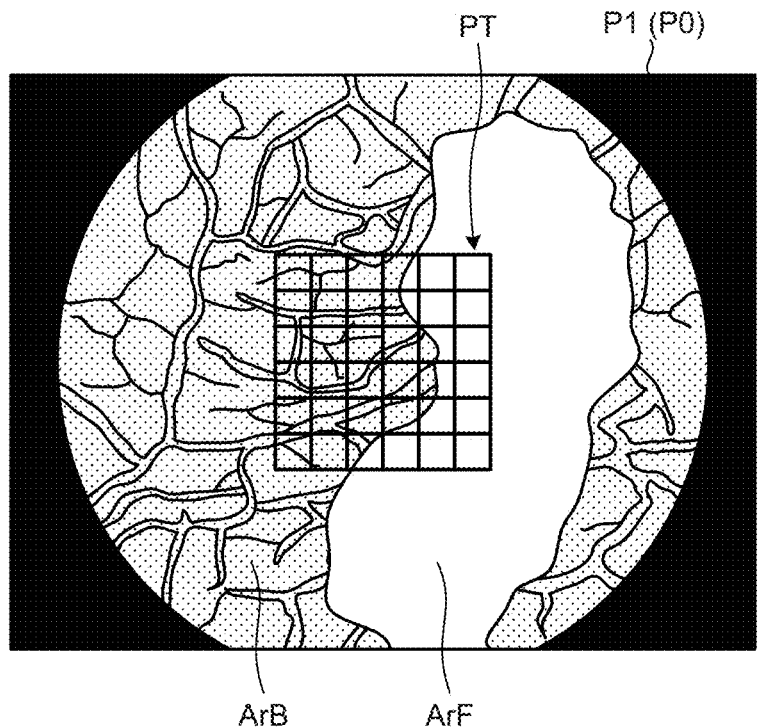
FIG. 7 is a view for explaining the operation of the control device.
Figure 8:
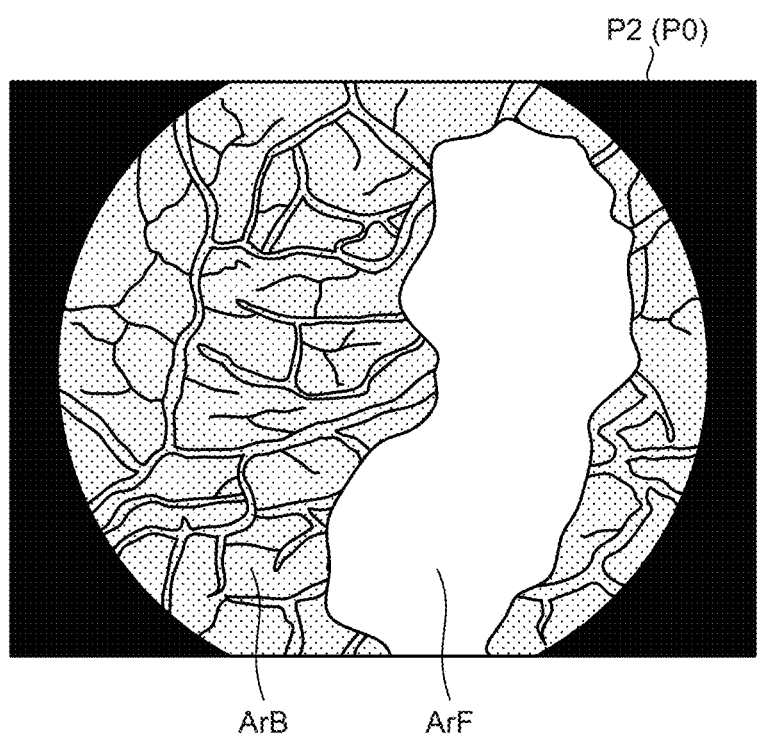
FIG. 8 is a view for explaining the operation of the control device.

FIG. 6 is a flowchart illustrating the operation of the control device 9. FIGS. 7 and 8 are views for explaining the operation of the control device 9. Specifically, FIGS. 7 and 8 are views illustrating a PDD image P0 of one frame generated by the image capturing unit 54. It should be noted that in FIGS. 7 and 8, a fluorescent area ArF represented by white corresponds to a lesion in which protoporphyrin excessively accumulates. Further, in FIGS. 7 and 8, a background area ArB other than the fluorescent area ArF is represented by dots. Here, FIG. 7 illustrates a PDD image P1 obtained by performing only the first image processing of the first and second image processing on the PDD image P0. On the other hand, FIG. 8 illustrates a PDD image P2 obtained by performing both the first and second image processing on the PDD image P0. Hereinafter, for convenience of explanation, the PDD image P1 is referred to as "pattern-containing PDD image P1", and the PDD image P2 is referred to as "processed PDD image P2".

First, the light source controller 931 simultaneously drives the first and second light source units 31, 32 (step S1). That is, the light source controller 931 simultaneously emits excitation light and the image light IL from the light source device 3 in step S1.

After step S1, the image capturing controller 932 causes the image sensor 542 to capture a subject image (excitation light, image light IL, and fluorescence) at a predetermined frame rate (step S2). The image capturing unit 54 then captures the subject image and sequentially generates the PDD image P0.

After step S2, the image processing unit 921 sequentially performs the first and second image processing on the PDD image P0 (step S3).

Here, in the PDD image P0 generated by the image capturing unit 54, the fluorescent area ArF is mainly composed of a fluorescent component (light component in red wavelength band). Further, in the PDD image P0, the background area ArB is mainly composed of an excitation light component (light component in blue wavelength band). Furthermore, since the subject image includes not only the excitation light and the fluorescence but also the image light IL, the PDD image P0 includes the pattern image PT as in the pattern-containing PDD image P1 illustrated in FIG. 7. Consequently, in the first embodiment, the light component in the second wavelength band included in the PDD image P0 (pattern-containing PDD image P1) is deleted. As a result, the processed PDD image P2 with the pattern image PT deleted is generated.

After step S3, the display controller 922 sequentially generates a video signal for displaying the processed PDD image, and sequentially outputs the video signal to the display device 7 (step S4). As a result, the processed PDD image P2 is sequentially displayed on the display device 7.

After step S4, the detection processing unit 923 performs the detection process based on the pixel information for each pixel in a specific detection area of the entire image area of the pattern-containing PDD image P1 (step S5). The detection area includes the image center of the pattern-containing PDD image P1, and includes at least a part of the pattern image PT. The detection processing unit 923 then outputs the detection information obtained by the detection process to the control unit 93.

After step S5, the evaluation value calculation unit 933 calculates an evaluation value (focusing evaluation value) based on the detection information obtained by the detection process in step S5 (step S6).

Specifically, the evaluation value calculation unit 933 calculates the focusing evaluation value for evaluating the focusing state of the image in the detection area of the entire image area of the pattern-containing PDD image P1 based on the detection information (contrast and frequency component) in step S6. For example, the evaluation value calculation unit 933 uses the contrast obtained by the detection process in step S5 or the sum of high-frequency components among the frequency components obtained by the detection process in step S5 as the focusing evaluation value. In the focusing evaluation value, the larger the value is, the more the focus is on.

As described above, the light source controller 931 controls the operation of the light source device 3 so that the captured image (pattern-containing PDD image P1) used for calculating the evaluation value (step S6) includes the component of the image light IL (pattern image PT).

After step S6, the focus position controller 934 performs an AF process of adjusting the focus position of the lens unit 51 (step S7).

Specifically, the focus position controller 934 refers to the focusing evaluation value calculated in step S6 and the current focus position detected by the focus position detection unit 53 in step S7. The focus position controller 934 then controls the operation of the lens driving unit 52 by hill climbing or the like while referring to the focusing evaluation value and the current focus position, so that the focus lens 511 is positioned at the focal position where the image in the detection area of the entire image area of the pattern-containing PDD image P1 is focused. As a result, the image in the detection area of the entire image area of the processed PDD image P2 is also focused.

Steps S5 to S7 described above are repeatedly performed in a specific cycle. That is, the "AF process" of the first embodiment is continuous AF that is repeatedly performed in a specific cycle. In other words, the evaluation value calculation unit 933 sequentially calculates the evaluation values used in the AF process in a specific cycle.

The first embodiment described above achieves the following effects.

The control device 9 of the first embodiment controls the operation of the light source device 3 so that the captured image (pattern-containing PDD image P1) used for calculating the evaluation value (step S6) includes the pattern image PT. That is, the control device 9 may calculate the evaluation value used in the AF process by using the pattern image PT with high contrast.

Consequently, the control device 9 of the first embodiment may appropriately calculate the evaluation value by calculating the evaluation value based on the pattern-containing PDD image P1, and may appropriately perform the AF process using the appropriate evaluation value. That is, an image suitable for observation may be generated.

Here, in the color filter 543, the G filter group 543g, which mainly transmits light in the green wavelength band, has more pixels than the R and B filter groups 543r, 543b, which mainly transmit light in the red and blue wavelength bands.

The image light IL including the pattern image PT is light in the green wavelength band. Consequently, the control device 9 may appropriately calculate the evaluation value used in the AF process by using the pattern image PT that is sufficiently bright and has high contrast.

Further, the control device 9 of the first embodiment performs the adjustment process of deleting the light component in the second wavelength band included in the PDD image P0 (pattern-containing PDD image P1). As a result, the processed PDD image P2 displayed on the display device 7 has the pattern image PT deleted and thus is suitable for observation.

Furthermore, the light in the second wavelength band of the present disclosure is light in a narrow band (light in green wavelength band) that does not include the wavelength band of fluorescence. That is, the color of the fluorescent area ArF (lesion) is not changed by the image light IL, and the lesion is easily seen, and thus an image suitable for observation may be generated.

Second Embodiment

Next, the second embodiment will be described.

In the following description, the same components as those in the first embodiment are designated by the same reference numerals, and detailed description thereof is omitted or simplified.

Figure 9:
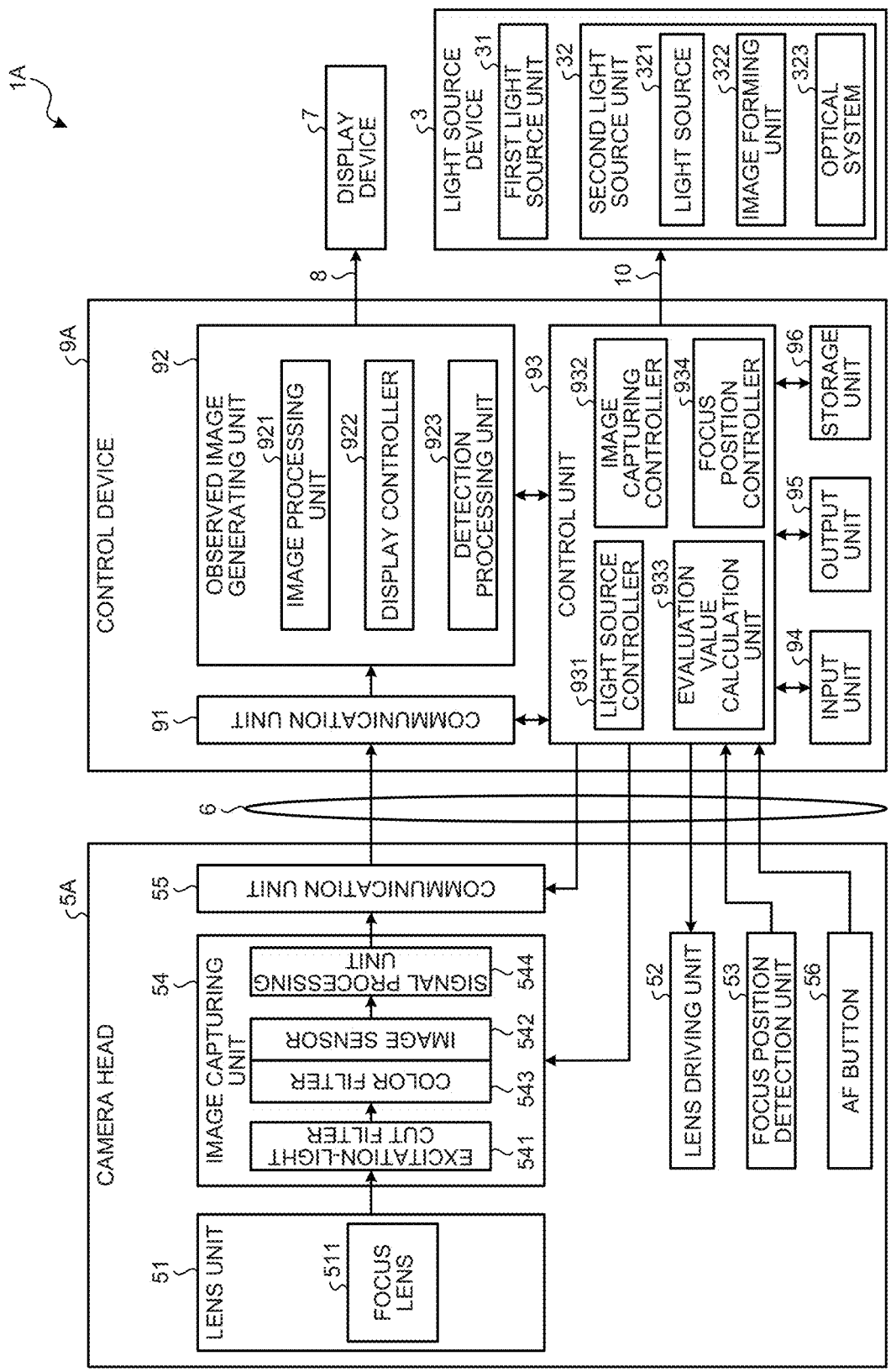
FIG. 9 is a block diagram illustrating a configuration of a medical observation system (camera head and control device) according to a second embodiment.

FIG. 9 is a block diagram corresponding to FIG. 4 and illustrating a configuration of a medical observation system 1A (camera head 5A and control device 9A) according to a second embodiment.

The control device 9 of the first embodiment described above performs continuous AF as "AF process".

On the other hand, the control device 9A of the second embodiment is provided in the camera head 5A, and performs the AF process in response to a user operation (pressing) on an AF button 56 (FIG. 9) that accepts the user operation to request the performance of the AF process. That is, the control device 9A performs one-touch AF as "AF process". The AF button 56 corresponds to an operation input unit of the present disclosure.

The camera head 5A of the second embodiment has a similar configuration to the camera head 5 described in the first embodiment, except that the AF button 56 is provided. Further, the control device 9A of the second embodiment has a similar configuration to the control device 9 described in the first embodiment described above, but is different from the control device 9 in the functions performed by the control unit 93.

Hereinafter, the functions performed by the control unit 93 will be described.

Figure 10:
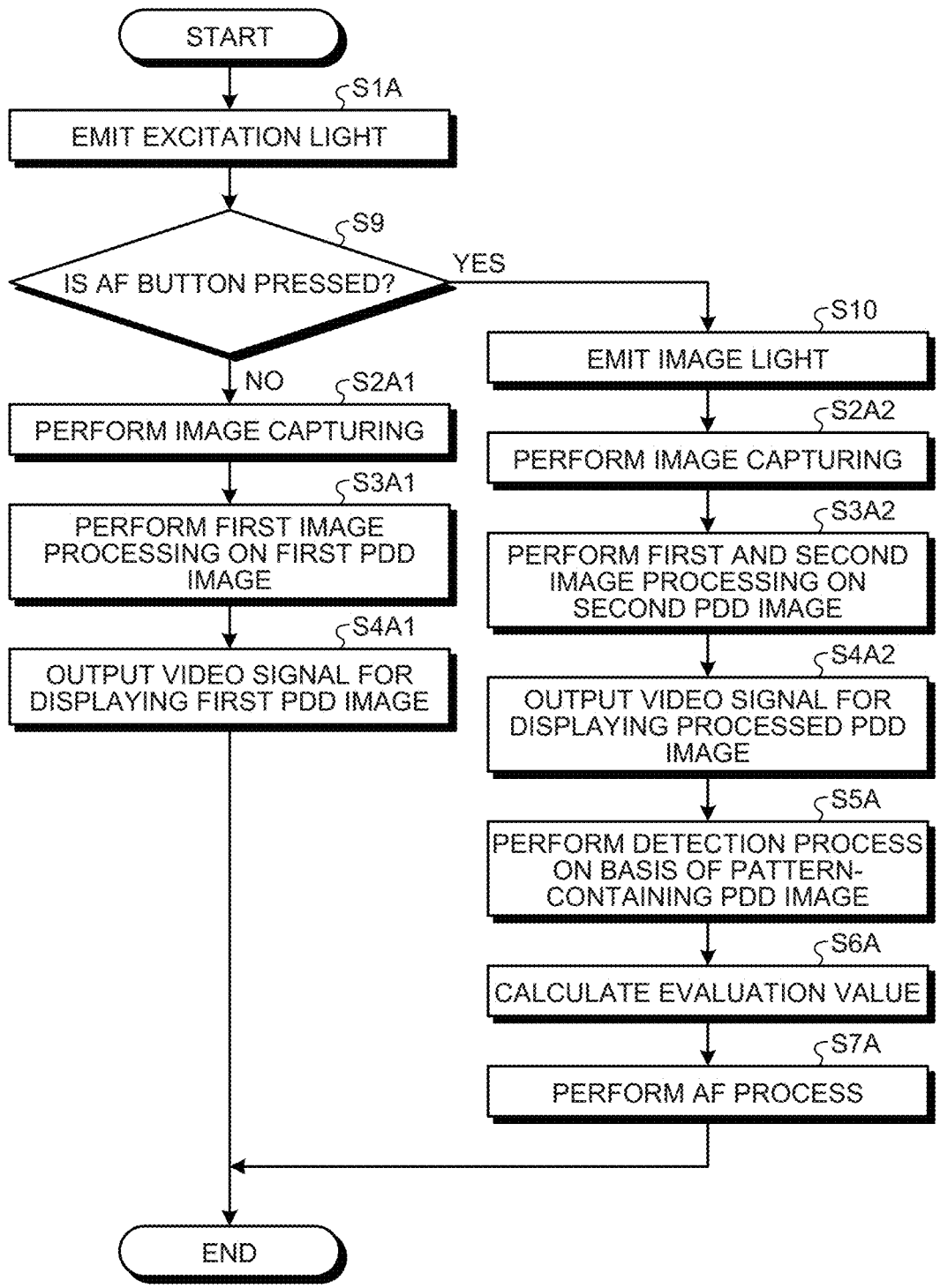
FIG. 10 is a flowchart illustrating an operation of the control device.

FIG. 10 is a flowchart illustrating an operation of the control device 9A.

First, the light source controller 931 drives the first light source unit 31 (step S1A). That is, the light source controller 931 emits only excitation light from the light source device 3 in step S1A. Consequently, only the excitation light is irradiated from the distal end of the insertion unit 2 to a living body. The excitation light that is irradiated to the living body and reflected in the living body and the fluorescence emitted by exciting protoporphyrin that accumulates in lesions in the living body is focused by the optical system in the insertion unit 2. Hereinafter, for convenience of explanation, the excitation light and the fluorescence focused by the optical system in the insertion unit 2 is referred to as "first subject image".

After step S1A, the control unit 93 determines whether or not the AF button 56 is pressed (step S9).

When it is determined that the AF button 56 is not pressed (step S9: No), the image capturing controller 932 causes the image sensor 542 to capture the first subject image (excitation light and fluorescence) at a predetermined frame rate. (step S2A1). The image capturing unit 54 then captures the first subject image and sequentially generates captured images. Hereinafter, for convenience of explanation, the captured image generated by capturing the first subject image (excitation light and fluorescence) with the image capturing unit 54 is referred to as "first PDD image". Since the image light IL is not emitted in step S1A, the first PDD image does not include the pattern image PT.

After step S2A1, the image processing unit 921 sequentially performs the first image processing on the first PDD image (step S3A1).

After step S3A1, the display controller 922 sequentially generates a video signal for displaying the first PDD image subjected to the first image processing, and sequentially outputs the video signal to the display device 7 (step S4A1). As a result, the first PDD image subjected to the first image processing is sequentially displayed on the display device 7.

On the other hand, when it is determined that the AF button 56 is pressed (step S9: Yes), the light source controller 931 drives the second light source unit 32 (step S10). That is, the light source controller 931 emits the image light IL in addition to excitation light from the light source device 3 in step S10. Consequently, the excitation light and the image light IL is emitted from the distal end of the insertion unit 2 to the living body. The excitation light that is irradiated to the living body and reflected in the living body, the image light IL that is reflected in the living body, and the fluorescence emitted by exciting protoporphyrin that accumulates in lesions in the living body is focused by the optical system in the insertion unit 2. Hereinafter, for convenience of explanation, the excitation light, the image light IL, and the fluorescence focused by the optical system in the insertion unit 2 is referred to as "second subject image". The second subject image is the same as the subject image described in the first embodiment described above.

After step S10, the image capturing controller 932 causes the image sensor 542 to capture the second subject image (excitation light, image light IL, and fluorescence) at a predetermined frame rate (step S2A2). The image capturing unit 54 then captures the second subject image and sequentially generates captured images. Hereinafter, for convenience of explanation, the captured image generated by capturing the second subject image (excitation light, image light IL, and fluorescence) with the image capturing unit 54 is referred to as "second PDD image".

After step S2A2, the image processing unit 921 sequentially performs the first and second image processing on the second PDD image (step S3A2).

The second PDD image subjected to the first and second image processing corresponds to the processed PDD image P2 described in the first embodiment described above. Further, the second PDD image subjected to only the first image processing of the first and second image processing corresponds to the pattern-containing PDD image described in the first embodiment described above.

After step S3A2, the control unit 93 performs steps S4A2, S5A, S6A, and S7A that are respectively similar to steps S4 to S7 described in the first embodiment described above.

That is, steps S5A, S6A, and S7A are performed only when the AF button 56 is pressed. Consequently, the "AF process" of the second embodiment is one-touch AF. In other words, the evaluation value calculation unit 933 calculates the evaluation value used in the AF process according to a user operation on the AF button 56.

As described above, in the second embodiment, the light source controller 931 controls the operation of the light source device 3 so that the captured image (pattern-containing PDD image P1) used for calculating the evaluation value (step S6A) includes the component of the image light IL (pattern image PT), as in the first embodiment described above.

The second embodiment described above achieves the following effect in addition to effects similar to those of the first embodiment described above.

The control device 9A of the second embodiment performs the adjustment process of deleting the light component in the second wavelength band (light in green wavelength band) included in the second PDD image. As a result, it is possible to prevent the pattern image PT from being included or not included in the PDD image displayed on the display device 7 depending on whether the AF process is performed with the one-touch AF or not, and thus the user such as a doctor does not have a strange feeling.

Third Embodiment

Next, the third embodiment will be described.

In the following description, the same components as those in the first embodiment are designated by the same reference numerals, and detailed description thereof is omitted or simplified.

Figure 11:
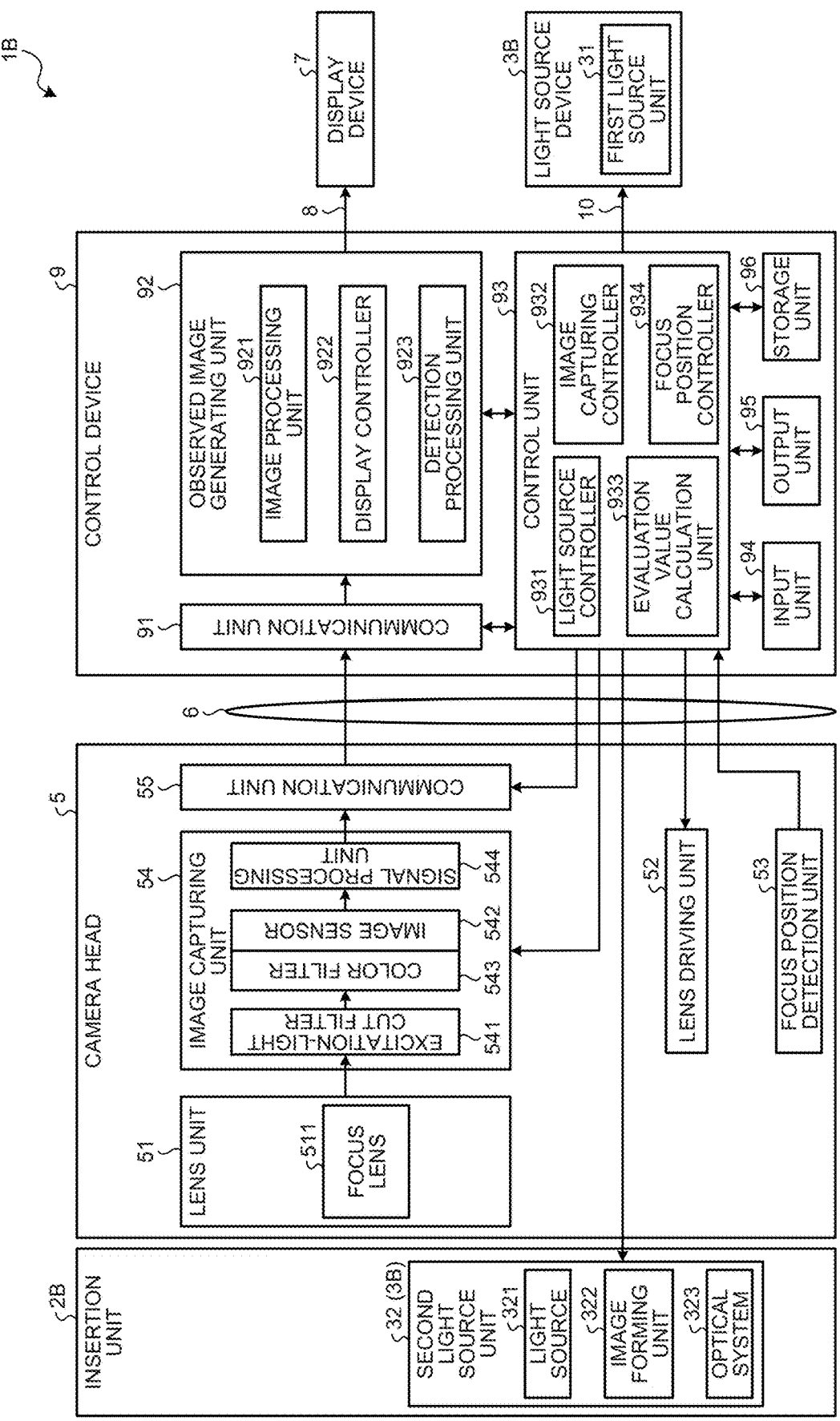
FIG. 11 is a block diagram illustrating a configuration of a medical observation system (insertion unit, camera head, and control device) according to a third embodiment.

FIG. 11 is a block diagram corresponding to FIG. 4 and illustrating a configuration of a medical observation system 1B (insertion unit 2B, camera head 5, and control device 9) according to a third embodiment.

In the medical observation system 1 according to the first embodiment described above, the image light IL emitted from the second light source unit 32 passes through the light guide 4 and the insertion unit 2 and then is irradiated to a living body.

On the other hand, in the medical observation system 1B (light source device 3B) according to the second embodiment, the second light source unit 32 is provided in the insertion unit 2 as illustrated in FIG. 11. The image light IL emitted from the second light source unit 32 is directly irradiated to the living body without passing through the light guide 4 and the insertion unit 2, under the control of the control device 9 (light source controller 931).

Even if the second light source unit 32 is configured as in the third embodiment described above, similar effects as those of the first embodiment described above are achieved.

Fourth Embodiment

Next, the fourth embodiment will be described.

In the following description, the same components as those in the first embodiment are designated by the same reference numerals, and detailed description thereof is omitted or simplified.

In the first embodiment described above, the present disclosure is applied to the medical observation system 1 using a rigid endoscope (insertion unit 2).

On the other hand, in the fourth embodiment, the present disclosure is applied to a medical observation system using a so-called videoscope having an image capturing unit on the distal end side of an insertion unit.

Figure 12:
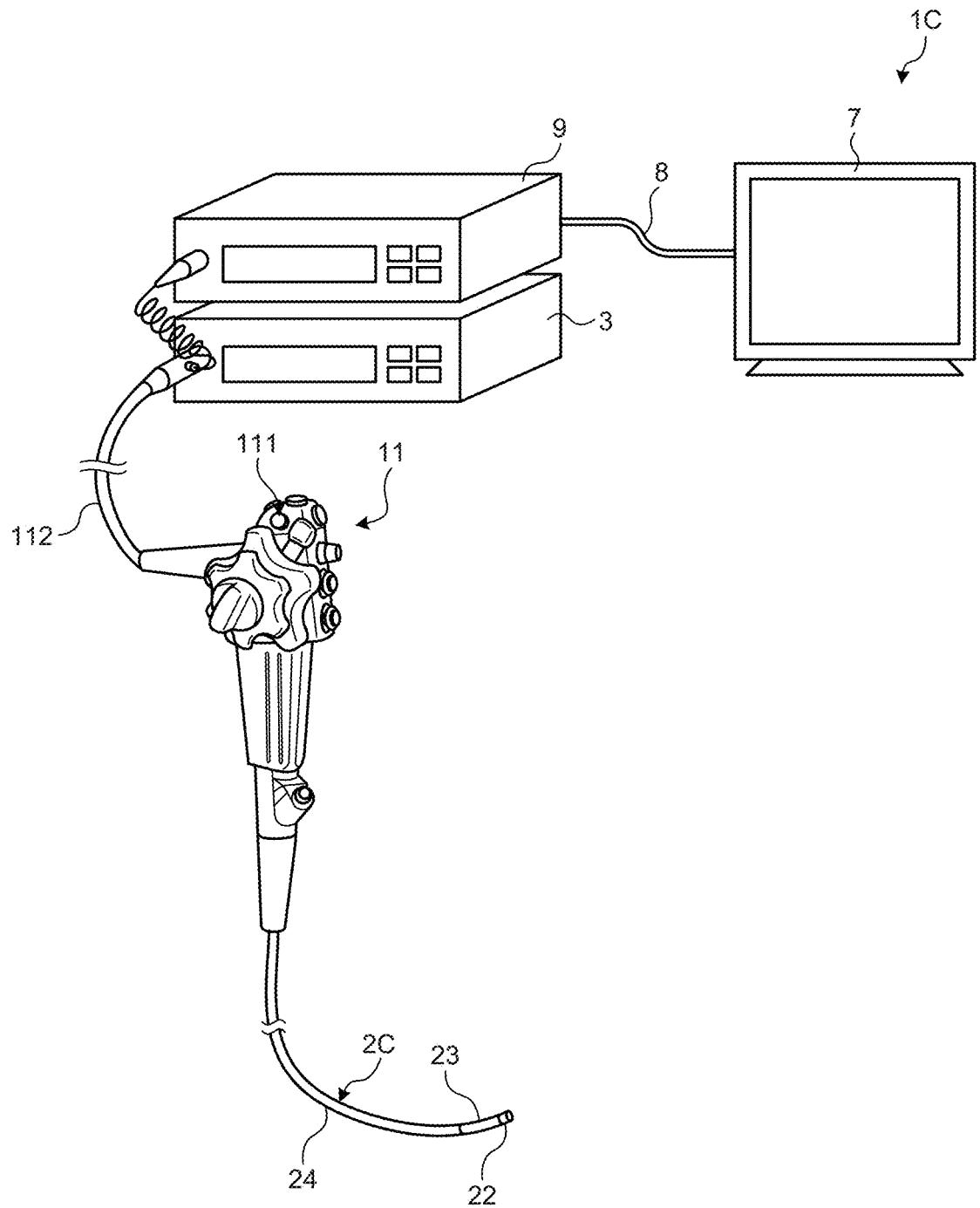
FIG. 12 is a view illustrating a configuration of a medical observation system according to a fourth embodiment.

FIG. 12 is a view illustrating a configuration of a medical observation system 1C according to the fourth embodiment.

As illustrated in FIG. 12, the medical observation system 1C according to the fourth embodiment includes an endoscope 11 that captures an in-vivo image of an observed region by inserting an insertion unit 2C into a living body and outputs an image signal, the light source device 3 that generates illumination light emitted from the distal end of the endoscope 11, the control device 9 that processes an image signal output from the endoscope 11, and the display device 7 that is connected to the control device 9 through the second transmission cable 8 and displays an image based on a video signal processed by the control device 9.

As illustrated in FIG. 12, the endoscope 11 includes the insertion unit 2C that is flexible and has an elongated shape, an operating unit 111 that is connected to the proximal end side of the insertion unit 2C and accepts various operations, and a universal cord 112 that extends from the operating unit 111 in a direction different from the direction in which the insertion unit 2C extends and contains various cables connected to the light source device 3 and the control device 9.

As illustrated in FIG. 12, the insertion unit 2C includes a distal end 22, a curved portion 23 that is connected to the proximal end side of the distal end 22 and is composed of a plurality of curved pieces so as to be curved, and a flexible tube portion 24 that is connected to the proximal end side of the curved portion 23, is flexible, and has an elongated shape.

A configuration substantially similar to that of the image capturing unit 54 described in the first embodiment described above is incorporated in the distal end 22, but its specific illustration is omitted. A configuration substantially similar to that of the communication unit 55 described in the first embodiment described above is incorporated in the operating unit 111, but its specific illustration is omitted. The image signal captured by the distal end 22 (image capturing unit) is output to the control device 9 via the operating unit 111 and the universal cord 112.

Even if the flexible endoscope (endoscope 11) is used as in the fourth embodiment described above, similar effects as those of the first embodiment described above are achieved.

Fifth Embodiment

Next, the fifth embodiment will be described.

In the following description, the same components as those in the first embodiment are designated by the same reference numerals, and detailed description thereof is omitted or simplified.

In the first embodiment described above, the present disclosure is applied to the medical observation system 1 using a rigid endoscope (insertion unit 2).

On the other hand, in the fifth embodiment, the present disclosure is applied to a medical observation system using a surgical microscope that enlarges and captures a predetermined visual field area of the inside (inside of living body) or surface (surface of living body) of a subject.

Figure 13:
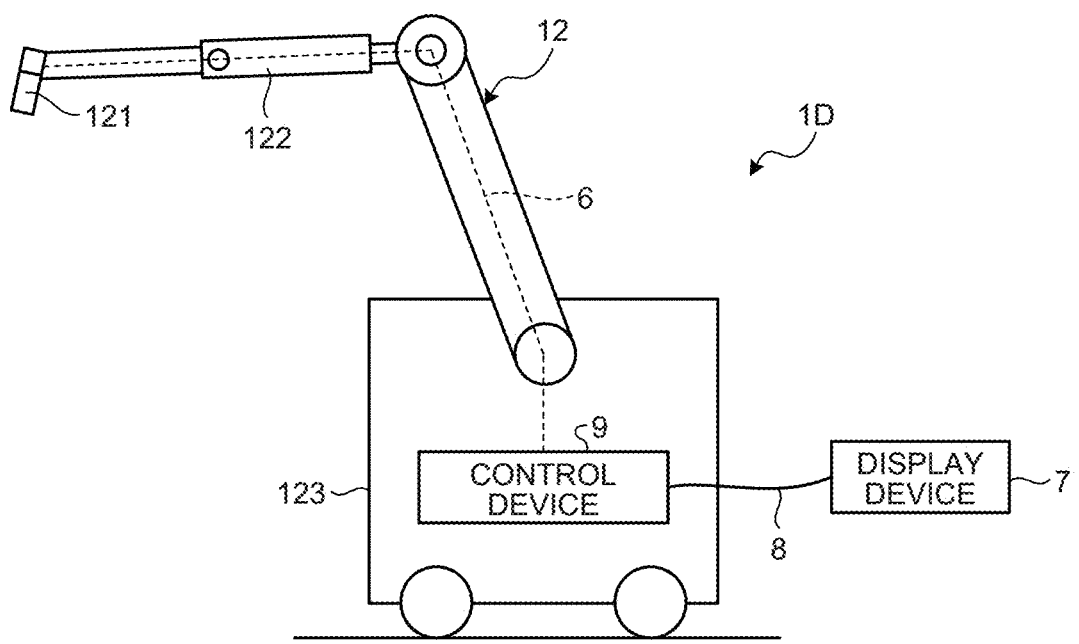
FIG. 13 is a view illustrating a configuration of a medical observation system according to a fifth embodiment.

FIG. 13 is a view illustrating a configuration of a medical observation system 1D according to the fifth embodiment.

As illustrated in FIG. 13, the medical observation system 1D according to the fifth embodiment includes a surgical microscope 12 that captures an image used for observing a subject and outputs an image signal, the control device 9 that processes an image signal output from the surgical microscope 12, and the display device 7 that is connected to the control device 9 through the second transmission cable 8 and displays an image based on a video signal processed by the control device 9.

As illustrated in FIG. 13, the surgical microscope 12 includes a microscope unit 121 that enlarges and captures a minute region of a subject and outputs an image signal, a support unit 122 that is connected to a proximal end portion of the microscope unit 121 and includes an arm rotatably supporting the microscope unit 121, and a base unit 123 that rotatably holds the proximal end portion of the support unit 122 and is movable on a floor surface.

The control device 9 is installed in the base unit 123 as illustrated in FIG. 13. Further, the light source device 3 that generates illumination light to be irradiated to the subject from the surgical microscope 12 is also installed in the base unit 123, but its specific illustration is omitted.

The base unit 123 does not need to be movably provided on the floor surface, and may be configured to be fixed to the ceiling, wall surface, or the like to support the support unit 122.

A configuration substantially similar to those of the image capturing unit 54 and the communication unit 55 described in the first embodiment described above is incorporated in the microscope unit 121, but its specific illustration is omitted. The image signal captured by the microscope unit 121 (image capturing unit) is then output to the control device 9 through the first transmission cable 6 arranged along the support unit 122.

Even if the surgical microscope 12 is used as in the fifth embodiment described above, similar effects as those of the first embodiment described above are achieved.

Other Embodiments

The modes for carrying out the present disclosure have been described above, but the present disclosure should not be limited only by the first to fifth embodiments described above.

In the first to fifth embodiments described above, the light source device 3 may emit light in the blue wavelength band as the excitation light in the first wavelength band, and may emit light in the green wavelength band as the image light IL, but the present disclosure is not limited thereto, and other light may be adopted as the excitation light in the first wavelength band and the image light IL.

For example, white light including light in the green wavelength band may be adopted as the light in the second wavelength band of the present disclosure. In this case, the first and second wavelength bands may partially overlap each other, or may not overlap at all.

Further, for example, the image light IL of the present disclosure is not limited to the image light formed by modulating the light in the green wavelength band, and may be formed by modulating the excitation light in the first wavelength band. In this case, the light source 321 may be omitted.

In the first to fifth embodiments described above, the pattern image of the present disclosure is not limited to the grid pattern image PT as long as it is an image of a specific pattern, and an image in which a plurality of straight lines are arranged in parallel, an image in which a plurality of wavy lines are arranged in parallel, and other images may be used.

The image forming unit 322 is used to form the pattern image PT in the first to fifth embodiments described above, but the present disclosure is not limited thereto. For example, it may be configured to form the pattern image PT by arranging a plurality of light emitting elements such as LEDs according to the pattern of the pattern image PT without using the image forming unit 322.

In the first to third embodiments described above, a part of the configuration of the camera heads 5 and 5A and a part of the configuration of the control devices 9 and 9A may be provided in the connector CN1 or the connector CN2, for example.

The following configurations also belong to the technical scope of the present disclosure.
(1) A medical control device including
circuitry configured to:
control an operation of a light source device configured to emit excitation light in a first wavelength band and image light including a specific pattern image;
acquire a captured image obtained by capturing an observation target irradiated with light emitted from the light source device;
calculate, based on the captured image, an evaluation value used in an autofocus process that controls a focus position of an imaging device configured to generate the captured image; and
perform the autofocus process based on the evaluation value, wherein
the circuitry is configured to control the operation of the light source device such that the pattern image is included in the captured image used for calculating the evaluation value.
(2) The medical control device according to (1), wherein
the image light includes light in a second wavelength band, and
the circuitry is further configured to perform an adjustment process of deleting a light component in the second wavelength band included in the captured image.
(3) The medical control device according to (2), wherein
the adjustment process is a white balance adjustment process, and
the light component in the second wavelength band is deleted by multiplying light components in red, green, and blue wavelength bands included in the captured image by a specific gain.
(4) The medical control device according to (2), wherein
the adjustment process is a color correction matrix process, and
the light component in the second wavelength band is deleted by multiplying an input matrix having light components in red, green, and blue wavelength bands included in the captured image as matrix elements by a specific color correction matrix.
(5) The medical control device according to (2), wherein
the adjustment process is a demosaic process, and when each pixel constituting the captured image includes light components in red, green, and blue wavelength bands, the light component in the second wavelength band is deleted by deleting a light component in any of the red, green, and blue wavelength bands.
(6) The medical control device according to any one of (2) to (5), wherein the light in the second wavelength band is light in a green wavelength band.
(7) The medical control device according to any one of (2) to (6), wherein the light in the second wavelength band is light that does not include a wavelength band of fluorescence from the observation target excited by the excitation light.
(8) The medical control device according to any one of (1) to (7), wherein the circuitry is configured to sequentially calculate an evaluation value used in the autofocus process in a specific cycle.
(9) The medical control device according to any one of (1) to (7), wherein the circuitry is configured to calculate an evaluation value used in the autofocus process in response to a user operation to an operation input unit to request the autofocus process.
(10) The medical control device according to any one of (1) to (9), wherein the excitation light is light in a blue wavelength band that excites protoporphyrin.
(11) The medical control device according to any one of (1) to (10), wherein the pattern image is a grid pattern image.
(12) A medical observation system including:
a light source device configured to emit excitation light in a first wavelength band and image light including a specific pattern image;
an imaging device configured to capture an observation target irradiated with light emitted from the light source device and generates a captured image; and
the medical control device according to any one of (1) to (11) configured to control operations of the light source device and the imaging device.

According to the medical image processing apparatus and the medical observation system according to the present disclosure, an image suitable for observation may be generated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A medical control device comprising
circuitry configured to:
control an operation of a light source device configured to emit excitation light in a first wavelength band and image light including a pattern image in a second wavelength band;
acquire a frame of a captured image obtained by capturing an observation target irradiated with light emitted from the light source device that fluoresces in response to the excitation light to output light in a third wavelength band, the frame of the captured image including light components in the second and third wavelengths bands, the second and third wavelength bands being different;
calculate, based on the pattern image of the second wavelength band in the frame of the captured image, an evaluation value used in an autofocus process that controls a focus position of an imaging device configured to generate the captured image; and perform the autofocus process based on the evaluation value.

2. The medical control device according to claim 1, wherein
the circuitry is further configured to delete a light component in the second wavelength band included in the captured image.

3. The medical control device according to claim 2, wherein
the circuitry is further configured to delete the light cornonent in the second wavelength band by a white balance adjustment process, and
the light component in the second wavelength band is deleted by multiplying light components in red, green, and blue wavelength bands included in the captured image by a. specific gain.

4. The medical control device according to claim 2, wherein
the circuitry is further configured to delete the light component in the second wavelength band by a color correction matrix process, and
the light component in the second wavelength band is deleted by multiplying an input matrix having light components in red, green, and blue wavelength bands included in the captured image as matrix elements by a specific color correction matrix.

5. The medical control device according to claim 2, wherein
the circuitry is further configured to delete the light component in the second wavelength band by a demosaic process, and
when each pixel constituting the captured image includes light components in red, green, and blue wavelength bands, the light component in the second wavelength band is deleted by deleting a light component in any of the red, green, and blue wavelength bands.

6. The medical control device according to claim 2, wherein the second wavelength band is a green wavelength band.

7. The medical control device according to claim 2, wherein the second wavelength band does not include the third wavelength band.

8. The medical control device according to claim 1, wherein the circuitry is configured to sequentially calculate the evaluation value used in the autofocus process in a specific cycle.

9. The medical control device according to claim 1, wherein the circuitry is configured to calculate the evaluation value used in the autofocus process in response to a user operation to an operation input unit to request the autofocus process.

10. The medical control device according to claim 1, wherein the excitation light is light in a blue wavelength band that excites protoporphyrin.

11. The medical control device according to claim 1, wherein the pattern image is a grid pattern image.

12. A medical observation system comprising:
a light source device configured to emit excitation light in a first wavelength band and image light including a specific pattern image;
an imaging device configured to capture an observation target irradiated with ligh emitted from the light source device and generates a captured image; and
the medical control device according to claim I configured to control operations of the light source device and the imaging device.

13. The medical control device according to claim 1, wherein the circuitry is configured to control the light source device to simultaneously emit excitation light in the first wavelength band and image light including the pattern image in the second wavelength band on condition that the autofocus process is to be performed.

14. The medical control device according to claim 1, wherein the second and third wavelength bands do not overlap.

15. The medical control device according to claim 14, wherein the first and second wavelength bands do not overlap.

16. The medical control device according to claim 1, wherein the first and second wavelength bands do not overlap.

* * * * *